(12) United States Patent
Hays et al.

(10) Patent No.: US 10,828,054 B2
(45) Date of Patent: Nov. 10, 2020

(54) SUBCUTANEOUS TUNNELING TOOL WITH DEPTH GUARD

(71) Applicant: Senseonics, Incorporated, Germantown, MD (US)

(72) Inventors: Bryan Hays, Germantown, MD (US); Abhi Chavan, Germantown, MD (US); Casey Haigh, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 137 days.

(21) Appl. No.: 16/230,272

(22) Filed: Dec. 21, 2018

(65) Prior Publication Data

US 2019/0192179 A1   Jun. 27, 2019

Related U.S. Application Data

(60) Provisional application No. 62/610,678, filed on Dec. 27, 2017.

(51) Int. Cl.
*A61B 17/32* (2006.01)
*A61B 17/34* (2006.01)
(Continued)

(52) U.S. Cl.
CPC .......... *A61B 17/32* (2013.01); *A61B 17/3415* (2013.01); *A61B 17/3468* (2013.01);
(Continued)

(58) Field of Classification Search
CPC ....... A61B 2017/320044; A61B 2017/320056; A61B 17/3494; A61B 2018/00464; A61B 2018/00452; A61B 2017/00747; A61B 17/32; A61B 17/34; A61N 1/0504; A47G 21/02; A47G 21/023; A47G 21/026; A61J 43/28; A61F 2002/0072; A61M 39/0208;
(Continued)

(56) References Cited

U.S. PATENT DOCUMENTS 3,939,562 A * 2/1976 Pellerin ................ A47G 21/026
                                                    30/147
5,304,187 A * 4/1994 Green ................... A61F 2/0063
                                                    604/13

(Continued)

FOREIGN PATENT DOCUMENTS

WO       2017/205675 A1    11/2017

*Primary Examiner* — Wade Miles
(74) *Attorney, Agent, or Firm* — Rothwell, Figg, Ernst & Manbeck, P.C.

(57) ABSTRACT

In one aspect, a tunneling tool for creating a subcutaneous pocket below a skin surface is provided. The tunneling tool may include a handle, a rod, a first prong, and a second prong. The rod and the first and second prongs may extend from a first end of the handle. The rod may extend farther from the first end of the handle than the first and second prongs and be configured to create the subcutaneous pocket. The first and second prongs may be configured to limit the depth at which the rod is capable of creating the subcutaneous pocket. The first and second prong may comprise first and second length indicators, respectively, configured to indicate a length of the subcutaneous pocket formed by the rod. In another aspect, a method of creating a subcutaneous pocket using the tunneling tool is provided.

28 Claims, 10 Drawing Sheets

(51) Int. Cl.
*A61N 1/05* (2006.01)
*A61B 17/3211* (2006.01)
*A61B 90/00* (2016.01)

(52) U.S. Cl.
CPC ............. *A61B 2017/320044* (2013.01); *A61B 2017/320056* (2013.01); *A61B 2017/32113* (2013.01); *A61B 2090/036* (2016.02); *A61B 2090/061* (2016.02); *A61B 2090/062* (2016.02); *A61N 1/0504* (2013.01)

(58) Field of Classification Search
CPC .. A61M 2202/0014; A61M 2202/0021; A61M 2202/0007
See application file for complete search history.

(56) References Cited

U.S. PATENT DOCUMENTS

| | | | | |
|---|---|---|---|---|
| 5,383,477 A * | 1/1995 | DeMatteis | A61B 17/0057 | |
| | | | 128/898 | |
| 5,411,511 A * | 5/1995 | Hall | A61F 9/0133 | |
| | | | 606/166 | |
| 5,458,579 A * | 10/1995 | Chodorow | A61B 17/3403 | |
| | | | 604/164.11 | |
| 5,460,612 A | 10/1995 | Madore | | |
| 5,542,181 A * | 8/1996 | Gaylord | A47G 21/02 | |
| | | | 30/148 | |
| 5,890,223 A * | 4/1999 | Klemmer | A47G 21/02 | |
| | | | 30/150 | |
| 6,030,402 A * | 2/2000 | Thompson | A61B 17/3494 | |
| | | | 606/105 | |
| 6,605,094 B1 | 8/2003 | Mann et al. | | |
| 6,974,450 B2 * | 12/2005 | Weber | A61B 18/1402 | |
| | | | 128/898 | |
| 8,133,216 B2 * | 3/2012 | Knopp | A61B 18/14 | |
| | | | 606/32 | |
| D823,072 S * | 7/2018 | Lefferts | D7/643 | |
| 2008/0091182 A1 * | 4/2008 | Mehta | A61B 18/1477 | |
| | | | 606/29 | |
| 2011/0034886 A1 | 2/2011 | Elbe et al. | | |
| 2011/0082479 A1 * | 4/2011 | Friedlander | A61F 2/0063 | |
| | | | 606/151 | |
| 2012/0288351 A1 * | 11/2012 | Nirmel | B66F 9/12 | |
| | | | 414/722 | |
| 2014/0059783 A1 * | 3/2014 | Lu | A47G 21/103 | |
| | | | 7/158 | |
| 2014/0310961 A1 * | 10/2014 | James | A47G 21/02 | |
| | | | 30/150 | |
| 2016/0106244 A1 * | 4/2016 | Michaels | A47G 21/04 | |
| | | | 30/150 | |
| 2017/0007053 A1 * | 1/2017 | Challa | A47G 21/02 | |
| 2018/0235591 A1 * | 8/2018 | Vendely | A61B 17/29 | |
| 2018/0360246 A1 * | 12/2018 | Lefferts | A47G 21/02 | |
| 2019/0380821 A1 * | 12/2019 | Childers, Jr. | A61B 17/3468 | |

* cited by examiner

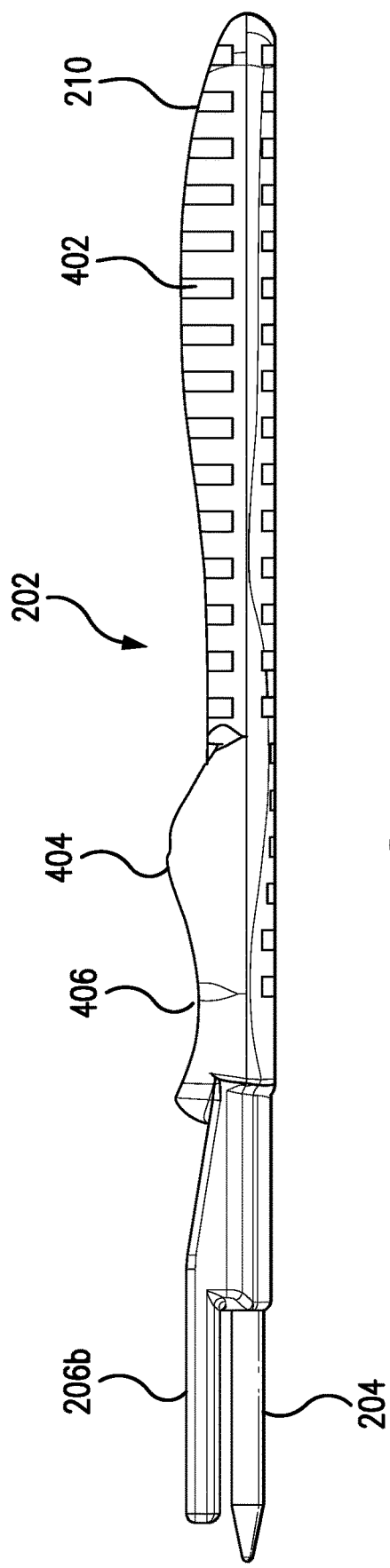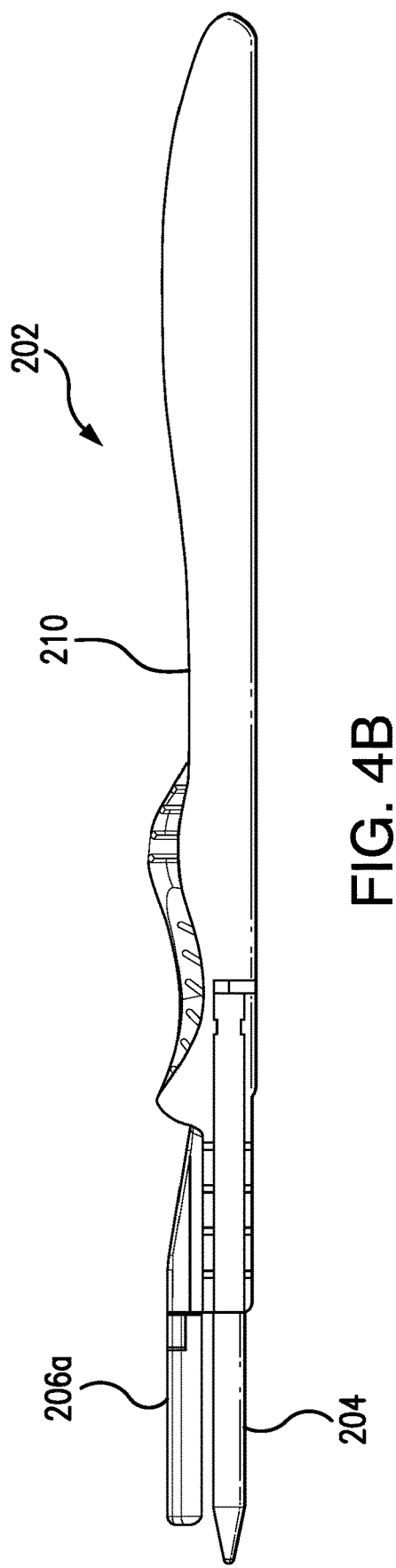
FIG. 4A
FIG. 4B

SUBCUTANEOUS TUNNELING TOOL WITH DEPTH GUARD

CROSS-REFERENCE TO RELATED APPLICATION

The present application claims the benefit of priority to U.S. Provisional Application Ser. No. 62/610,678, filed on Dec. 27, 2017, which is incorporated herein by reference in its entirety.

BACKGROUND

Field of Invention

This disclosure relates to a tunneling tool for creating a subcutaneous pocket below a skin surface for the implantation of sensors.

Discussion of the Background

Implantable sensors may be implanted within a living animal (e.g., a human) and may detect the presence or amount of an analyte (e.g., glucose or oxygen) in a medium (e.g., blood or interstitial fluid) within the living animal. Some implantable sensors are implanted in subcutaneous tissue below the skin. The subcutaneous insertion of a sensor is a relatively simple procedure and may take less than five minutes.

Known tools for inserting a sensor in subcutaneous tissue may include a tunneling tool and an insertion tool. In some embodiments, the tunneling tool may be used to create a subcutaneous pocket below a skin surface, and the insertion tool may be used to insert the sensor into the pocket.

A sensor inserted in a pocket created too deep underneath the skin or at a non-zero angle to the surface of the skin may be unable to maintain consistent communication with a reader positioned above the inserted sensor on or near the surface of the skin and configured to receive sensed information from the sensor. Furthermore, a sensor inserted in a pocket created too deep underneath the skin may be significantly more difficult to remove.

Accordingly, there is a need for an improved tunneling device to reduce the variability (e.g., depth and angle) of a subcutaneous pocket created below a skin surface.

SUMMARY

Aspects of the present invention relate to an improved tunneling device to reduce the variability of sensor insertion depth under the skin.

One aspect of the invention may provide a tunneling tool for creating a subcutaneous pocket below a skin surface. The tunneling tool may include a handle, a rod, and first and second prongs. In some embodiments, the rod may extend from a first end of the handle and configured to create the subcutaneous pocket. In some embodiments, the first and second prongs may extend from the first end of the handle. The first and second prongs may be configured to limit the depth at which the rod is capable of creating the subcutaneous pocket. The rod may extend farther from the first end of the handle than the first and second prongs. In some embodiments, a first gap between the rod and the first prong and a second gap between the rod and the second prong are configured to limit the angle relative to the skin surface at which rod is capable of forming the subcutaneous pocket.

In some embodiments, the first prong may comprise a first length indicator configured to indicate a length of the subcutaneous pocket formed by the rod. In some embodiments, the second prong may comprise a second length indicator configured to indicate a length of the subcutaneous pocket formed by the rod. The first prong and the second prong may have the same length. In some embodiments, the first prong and the second prong may be configured to prevent damage to the skin surface.

In some embodiments, the rod may comprise a dull tip. In some embodiments, the handle may comprise a bottom surface and the first and the second prongs may be located above the rod in a plane substantially parallel to the bottom surface of the handle. In some embodiments, the first prong may be located at a first angle to the rod and the second prong may be located at a second angle to the rod.

In some embodiments, the handle may comprise a top surface including a circular depression configured to accommodate a finger. The top surface of the handle may further include at least one or more ridges configured to accommodate another finger and a thumb. In some embodiments, the top surface of the handle may comprise a ribbed surface.

Another aspect of the invention may provide a method of creating a subcutaneous pocket below a skin surface. The method may include creating an incision in the skin surface. The method may include inserting a tip of a rod extending from a first end of a handle of a tunneling tool into the incision until one or more of first and second prongs extending from the first end of the handle of the tunneling tool contact the skin surface. In some embodiments, the first and second prongs may limit the depth at which the rod is capable of creating the subcutaneous pocket. The method may include reducing an angle between the tunneling tool and the skin surface by rotating the tunneling tool while the tip of the rod remains inserted in the incision. After reducing the angle between the tunneling tool and the skin surface, the method may include inserting the rod further into the incision such that the rod passes below the skin surface, the first and second prongs pass over the skin surface, the skin surface is disposed in a first gap between the rod and the first prong, and the skin surface is disposed in a second gap between the rod and the second prong. In some embodiments, the first and second gaps may be configured to limit the angle relative to the skin surface at which rod is capable of forming the subcutaneous pocket.

In some embodiments, the method may further include continuing to insert the rod into the incision until the incision is aligned with a first length indicator on the first prong. In some embodiments, the method may further include continuing to insert the rod into the incision until the incision is aligned with a second length indicator on the second prong. In some embodiments, inserting the rod further into the incision may include rocking the tunneling tool side to side thereby creating a rotating motion along a longitudinal axis of the rod to facilitate the insertion. The handle may comprise a bottom surface and the first and the second prongs may be located above the rod in a plane substantially parallel to the bottom surface of the handle. The first prong may be located at a first angle to the rod and the second prong may be located at a second angle to the rod. In some embodiments, the location of the first and second prong in relation to the rod may facilitate rocking the tunneling tool side to side.

Another aspect of the invention may provide a tunneling tool for creating a subcutaneous pocket below a skin surface. The tunneling tool may include a handle, a rod, and first and second prongs. In some embodiments, the rod may extend from a first end of the handle and configured to create the subcutaneous pocket. In some embodiments, the first and second prongs may extend from the first end of the handle. The first prong may comprise a first length indicator configured to indicate a length of the subcutaneous pocket formed by the rod and the second prong may comprise a second length indicator configured to indicate the length of the subcutaneous pocket formed by the rod. The rod may extend farther from the first end of the handle than the first and second prongs. In some embodiments, a first gap between the rod and the first prong and a second gap between the rod and the second prong are configured to limit the angle relative to the skin surface at which rod is capable of forming the subcutaneous pocket.

In some embodiments, the first prong and the second prong may have the same length. In some embodiments, the first prong and the second prong may be configured to prevent damage to the skin surface.

In some embodiments, the rod may comprise a dull tip. In some embodiments, the handle may comprise a bottom surface and the first and the second prongs may be located above the rod in a plane substantially parallel to the bottom surface of the handle. In some embodiments, the first prong may be located at a first angle to the rod and the second prong may be located at a second angle to the rod.

In some embodiments, the handle may comprise a top surface including a circular depression configured to accommodate a finger. The top surface of the handle may further include at least one or more ridges configured to accommodate another finger and a thumb. In some embodiments, the top surface of the handle may comprise a ribbed surface.

Another aspect of the invention may provide a method of creating a subcutaneous pocket below a skin surface. The method may include creating an incision in the skin surface. The method may include inserting a tip of a rod extending from a first end of a handle of a tunneling tool into the incision until one or more of first and second prongs extending from the first end of the handle of the tunneling tool contact the skin surface. The method may include reducing an angle between the tunneling tool and the skin surface by rotating the tunneling tool while the tip of the rod remains inserted in the incision. After reducing the angle between the tunneling tool and the skin surface, the method may include inserting the rod further into the incision such that the rod passes below the skin surface, the first and second prongs pass over the skin surface, the skin surface is disposed in a first gap between the rod and the first prong, and the skin surface is disposed in a second gap between the rod and the second prong. In some embodiments, the first and second gaps may be configured to limit the angle relative to the skin surface at which rod is capable of forming the subcutaneous pocket. The method may include continuing to insert the rod into the incision until the incision is aligned with at least one of a first length indicator on the first prong and a second length indicator on the second prong. In some embodiments, the first length indicator may indicate a length of the subcutaneous pocket formed by the rod and the second length indicator may indicate the length of the subcutaneous pocket formed by the rod.

In some embodiments, the method may further include continuing to insert the rod into the incision until the incision is aligned with a second length indicator on the second prong. In some embodiments, inserting the rod further into the incision may include rocking the tunneling tool side to side thereby creating a rotating motion along a longitudinal axis of the rod to facilitate the insertion. The handle may comprise a bottom surface and the first and the second prongs may be located above the rod in a plane substantially parallel to the bottom surface of the handle. The first prong may be located at a first angle to the rod and the second prong may be located at a second angle to the rod. In some embodiments, the location of the first and second prong in relation to the rod may facilitate rocking the tunneling tool side to side.

Other features and characteristics of the subject matter of this disclosure, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures

BRIEF DESCRIPTION OF THE DRAWINGS

The accompanying drawings, which are incorporated herein and form part of the specification, illustrate various embodiments of the subject matter of this disclosure. In the drawings, like reference numbers indicate identical or functionally similar elements.

FIG. 4A is a side view of the tunneling tool embodying aspects of the present disclosure.

FIG. 4B is a cross-sectional side view of the tunneling tool embodying aspects of the present disclosure.

DETAILED DESCRIPTION

Figure 1:
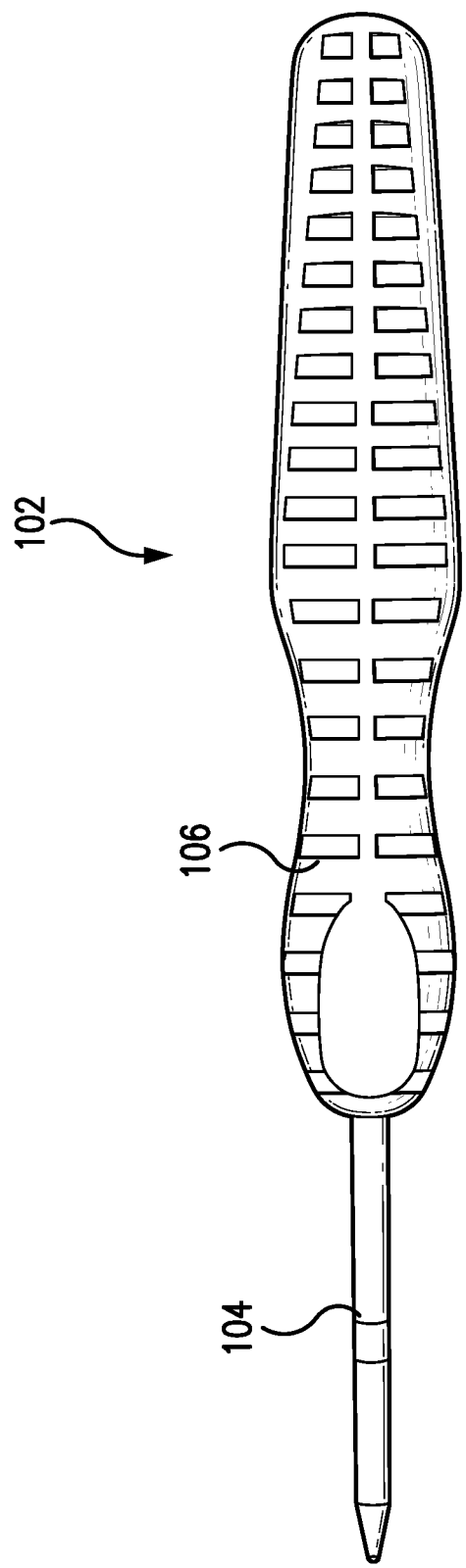
FIG. 1 is a top view of a conventional tunneling tool.

FIG. 1 illustrates an example of the conventional tunneling tool 102 for creating a subcutaneous pocket below a skin surface. As illustrated in FIG. 1, the conventional tunneling tool 102 may have a rod/shaft 104 extending from a handle 106. The conventional tunneling tool 102 requires the experienced handling of a trained physician or other clinician to create a subcutaneous pocket at the appropriate depth below and parallel to the skin surface. However, even a trained clinician may make mistakes, and the conventional tunneling tool 102 does not effectively restrict the clinician from creating inadvertently the subcutaneous pocket at a non-zero angle to the surface of the skin and/or creating a pocket too deep below the surface of the skin.

The embodiments described in the present disclosure may obviate one or more of the above noted problems with the conventional tunneling tool 102. Specifically, the embodiments described in the present disclosure may provide the advantages of creating a subcutaneous pocket that is parallel to a surface of the skin and not created too deep underneath the surface of the skin.

Figure 2:
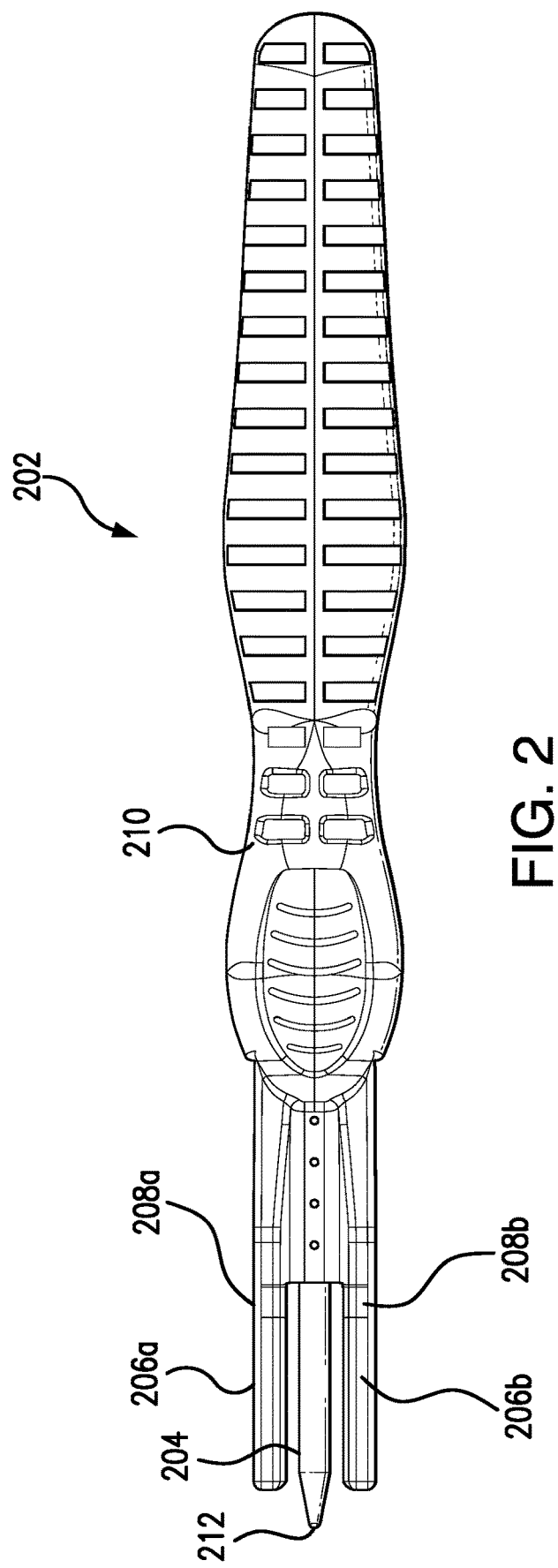
FIG. 2 is a top view of a tunneling tool embodying aspects of the present disclosure.

FIG. 2 is top view of a tunneling tool 202 embodying aspects of the present disclosure. In some embodiments, the tunneling tool 202 may include a handle 210, a rod/shaft 204 (referred to as "rod" hereinafter) extending from an end of the handle 210, and first and second prongs 206a and 206b extending from the end of the handle 210. In some embodiments, the first and second prongs 206a-b may be integrally formed in the handle 210. In some non-limiting embodiments, the first and second prongs 206a-b may be integrally formed in the handle 210, for example and without limitation, with the handle 210 comprising a single plastic overmold. In some embodiments, the rod 204 may include a trocar. In some non-limiting embodiments, the trocar may be, for example and without limitation, a steel trocar (e.g., a stainless steel trocar) or made of another material suitable for surgical tools.

In some embodiments, as illustrated in FIG. 2, the rod 204 may extend farther from the end of the handle 210 than the first and second prongs 206a-b. In some embodiments, in operation, a tip 212 of the rod 204 may be inserted into an incision made in a skin surface. In some embodiments, the incision may be, for example and without limitation, 6-8 mm wide and 4-6 mm deep. In some embodiments, the first prong 206a and the second prong 206b may function as depth guards configured to limit the depth at which the rod 204 is inserted into the skin surface. Accordingly, the length of the first prong 206a and the second prong 206b may be configured to physically prevent the rod 204 from being inserted too deep beneath the surface of the skin, thereby preventing the creation of a subcutaneous pocket too far below the surface of the skin. In some embodiments, the length of the first prong 206a and length of the second prong 206b may be the same. In some non-limiting embodiments, the length of the first prong 206a and the second prong 206b may be, for example and without limitation, 35 mm. In some non-limiting embodiments, the rod 204 may extend beyond the ends of the first and second prongs 206a-b by, for example and without limitation, 5 mm. However, these specific lengths and dimensions are not required, and some alternative embodiments may use different lengths and/or dimensions.

In some embodiments, one or more of the first and second prongs 206a-206b may include a length indicator. In some non-limiting embodiments, as shown in FIG. 2, the first and second prongs 206a and 206b may include first and second length indicators 208a and 208b, respectively. In some embodiments, in operation, the tunneling tool 202 may be rotated with the tip 212 of the rod 204 inserted in the incision made in the skin surface to reduce an angle between the tunneling tool 202 and the skin surface, i.e., to reduce an entry angle for the tunneling tool 202. That is, the tunneling tool 202 may be rotated with the tip 212 of the rod 204 inserted in the incision to reduce the entry angle of the tunneling tool 202. In some embodiments, the tunneling tool 202 may be rotated until a bottom surface of the tunneling tool 202 contacts the skin surface. In some embodiments, rotating the tunneling tool 202 until the bottom surface of the tunneling tool 202 contacts the skin surface may minimize the entry angle between the bottom surface of the tunneling tool 202 and the skin surface.

In some embodiments, in operation, after reducing the angle between the tunneling tool 202 and the skin surface (e.g., by rotating the tunneling tool 202), the rod 204 may be inserted further into the incision such that the rod 204 passes below the skin surface, and the skin surface is disposed between the rod 204 and the first and second prongs 206a-b. In such embodiments, the first length indicator 208a and the second indicator 208b may indicate a length of the subcutaneous pocket formed by the rod 204. In some embodiments, the first and second length indicators 208a-b may include a contrasting color, ridge shape, indentation or a combination to be distinguishable from the handle 210. In some embodiments, the first and second length indicators 208a-b may be located on a top surface of the first and second prongs 206a-b, respectively. In such embodiments, the first and second length indicator 208a-b may be visible to a user during use of the tunneling tool 202, e.g., while inserting the rod 204 into an incision in the skin surface such that the rod 204 passes below the skin surface and the skin surface is disposed between the rod 204 and the first and second prongs 206a-b. In some non-limiting embodiments, the first and second length indicator 208a-b may be printed onto the top surface of the first and second prongs 206a-b, respectively.

In some embodiments, the rod 204 may include a tip 212 at the end of the rod 204. In some embodiments, the tip 212 may be a dull tip. In some embodiments, the dull tip 212 of the rod 204 may enable the rod 204 to create space between layers of tissue underneath the skin surface. In some embodiments, the dull tip 212 may prevent the rod 204 from being able to pierce through vital tissue in the portion of the living animal (e.g., wrist, arm, leg, or abdomen) in which the subcutaneous pocket is being created.

Figure 3:
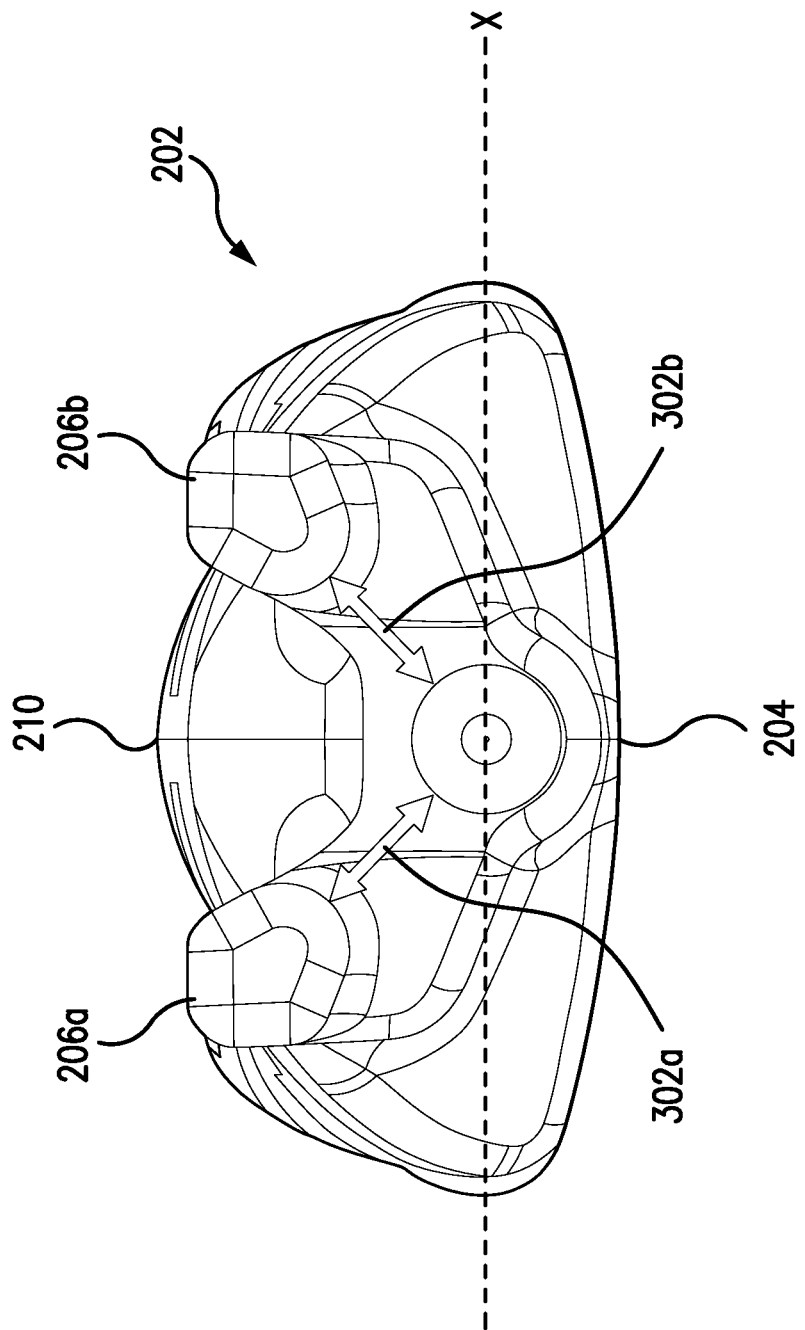
FIG. 3 is a front view of the tunneling tool embodying aspects of the present disclosure.

FIG. 3 is a front view of the tunneling tool 202 embodying aspects of the present disclosure. In some embodiments, as illustrated in FIG. 3, the first and second prongs 206a-b may be located above the rod 204 in a plane substantially parallel to a bottom surface of the handle 210. In some embodiments, the tunneling tool 202 may include a first gap 302a between the first prong 206a and the rod 204 and a second gap 302b between the second prong 206b and the rod 204. In some embodiments, the first prong 206a and the second prong 206b may each be located at an angle from the rod 204 with respect to the x-axis, as shown in FIG. 3. For example and without limitation, the first prong 206a and the second prong 206b may each be located at a 45 degree angle from the rod 204 with respect to the x-axis. However, it is not required that the first prong 206a and the second prong 206b be located at 45 degree angles, and one or more of the first and second prong 206a-b may be located at a different angle with respect to the x-axis in some alternative embodiments. As described above, in some embodiments, the rod 204 may be inserted into the incision such that the rod 204 passes below the skin surface. In such embodiments, the skin surface may be disposed in the first gap 302a between the rod 204 and the first prong 206a and between the rod 204 and in the second gap 302b between the second prong 206b. The location of the first and second prongs 206a-b with respect to the rod 204 (e.g., the angle formed between each of the prongs 206a-b and the rod 204) may enable a user to rock the tunneling tool 202 side to side while inserting the rod 204 further into the incision. Rocking the tunneling tool 202 side to side may create a rotating motion along a longitudinal axis of the rod 204. Rocking the tunneling tool 202 may thereby provide a controlled insertion of the rod into the incision and prevent the rod 204 from piercing through vital tissue during the insertion. In some embodiments, the first and second gaps 302a-b may be uniform throughout the length of the first and second prongs 206a-b. According to some embodiments, the first and second gaps 302a-b may limit the angle (relative to the skin surface) of the subcutaneous pocket created by the insertion of the rod 204 into the incision. In some embodiments, the first and second gap 302a-b may enable the rod 204 to create a subcutaneous pocket substantially parallel to the surface of the skin. In some embodiments, the first and second prongs 206a-b may be configured to prevent damage to the skin, such as a puncture, due to misuse of the tunneling tool 202. In some non-limiting embodiments, the first prong 206a and the second prong 206b may comprise a smooth rounded surface, which may prevent damage to the skin.

FIG. 4A is a side view of the tunneling tool 202 embodying aspects of the present disclosure. In some embodiments, as illustrated in FIG. 4A, the tunneling tool 202 may include a side grip 404 on one or both sides of the handle 210. In some embodiments, the tunneling tool 202 may include one or more of a bump 402 on a top surface the handle 210 and a depression 406 formed on the top surface of the handle 210. In some embodiments, in operation, the tunneling tool 202 may be gripped by a user so that a thumb contacts a side grip 404 on one side of the tunneling tool 202 while a middle finger contacts a side grip 404 on the other side of the tunneling tool 202. In some embodiments, the side grip 404 may include one or more ridges configured to accommodate a finger and a thumb. In some embodiments, the bump 402 may fit into a palm of a user's hand when using the tunneling tool 202. In some embodiments, a user's index finger may fit into the depression 406 formed on the top surface of the handle 210. In some embodiments, the depression 406 may have a circular or oval form configured to accommodate a finger. In some embodiments, the handle 210 may include a ribbed top surface to enhance friction between the user's hand and the handle.

Figure 4C:
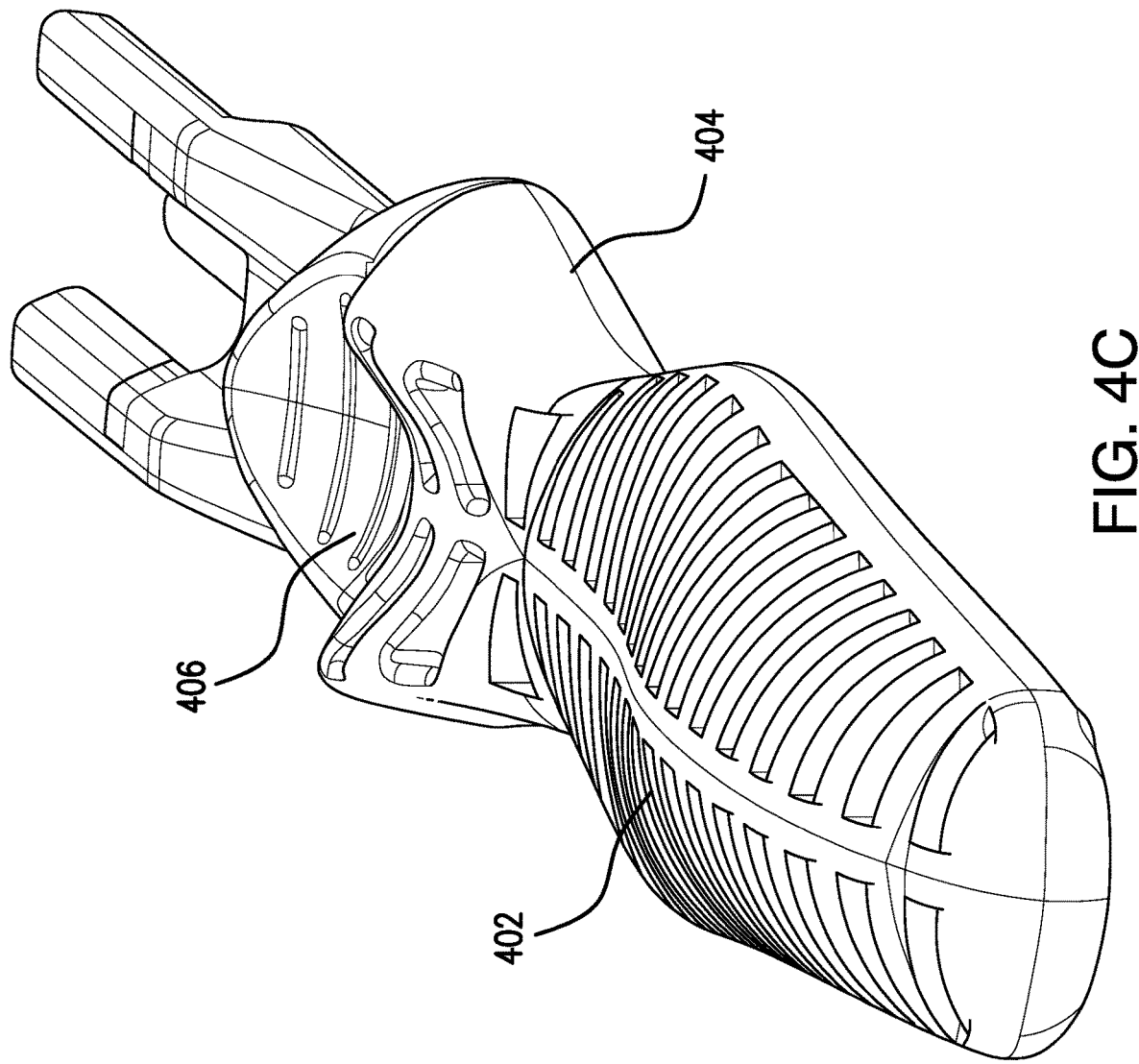
FIG. 4C is a perspective view of the tunneling tool embodying aspects of the present disclosure.
Figure 4D:
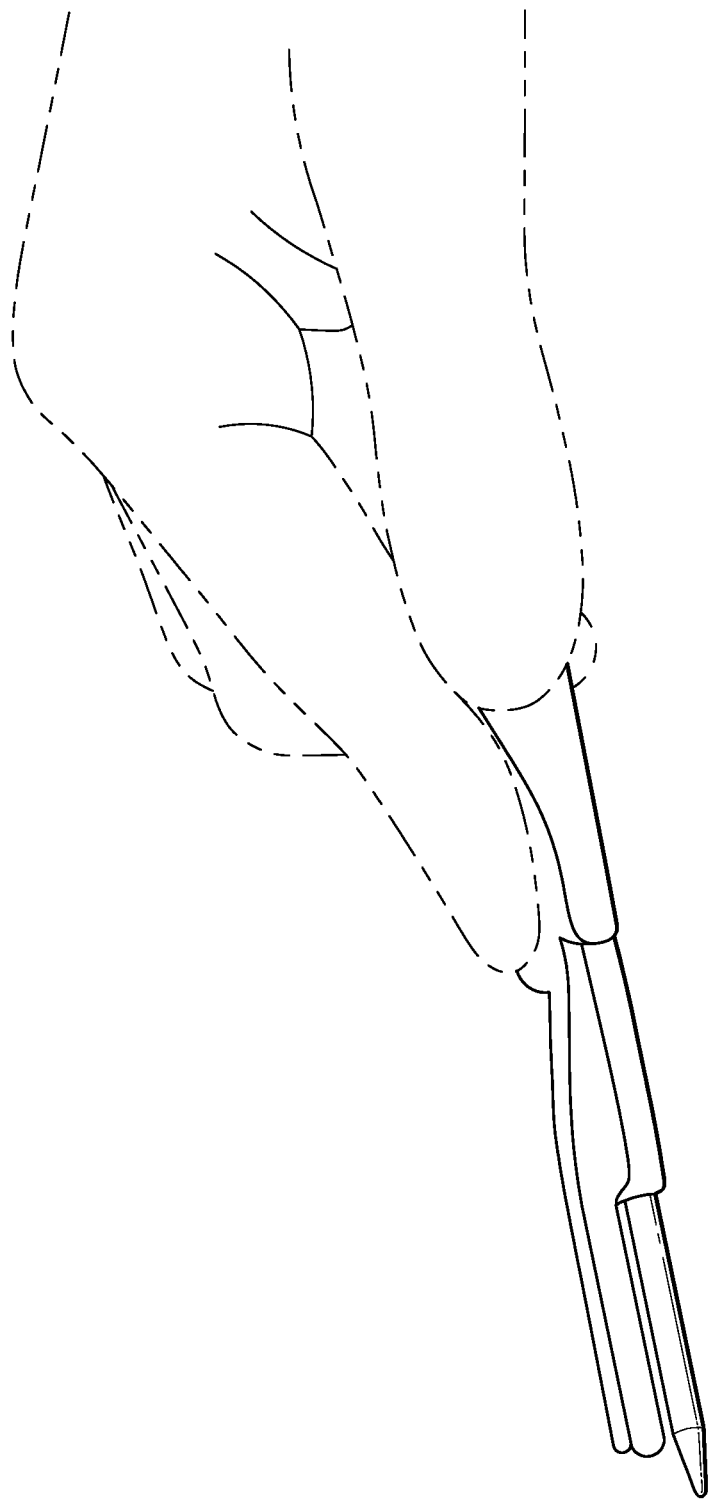
FIG. 4D is an illustration of the tunneling tool held by a user, according to embodiments of the present disclosure.

FIG. 4B is a cross-sectional side view of the tunneling tool 202 embodying aspects of the present disclosure. In some embodiments, as illustrated in FIG. 4B, the handle 210 may be molded around an end of the rod 204 to securely hold the rod in place. In some embodiments, the molded over portion of the handle 210 may determine the length of the rod 204 extending from an end of the handle. In some embodiments, the first and second prongs 206a-b may be integrally formed with the handle 210 comprising a single overmold. FIG. 4C is a perspective view of the tunneling tool 202 embodying aspects of the present disclosure. FIG. 4D provides an illustration of the tunneling tool 202 gripped by a user, according to embodiments described in FIGS. 4B-C.

Figure 5A:
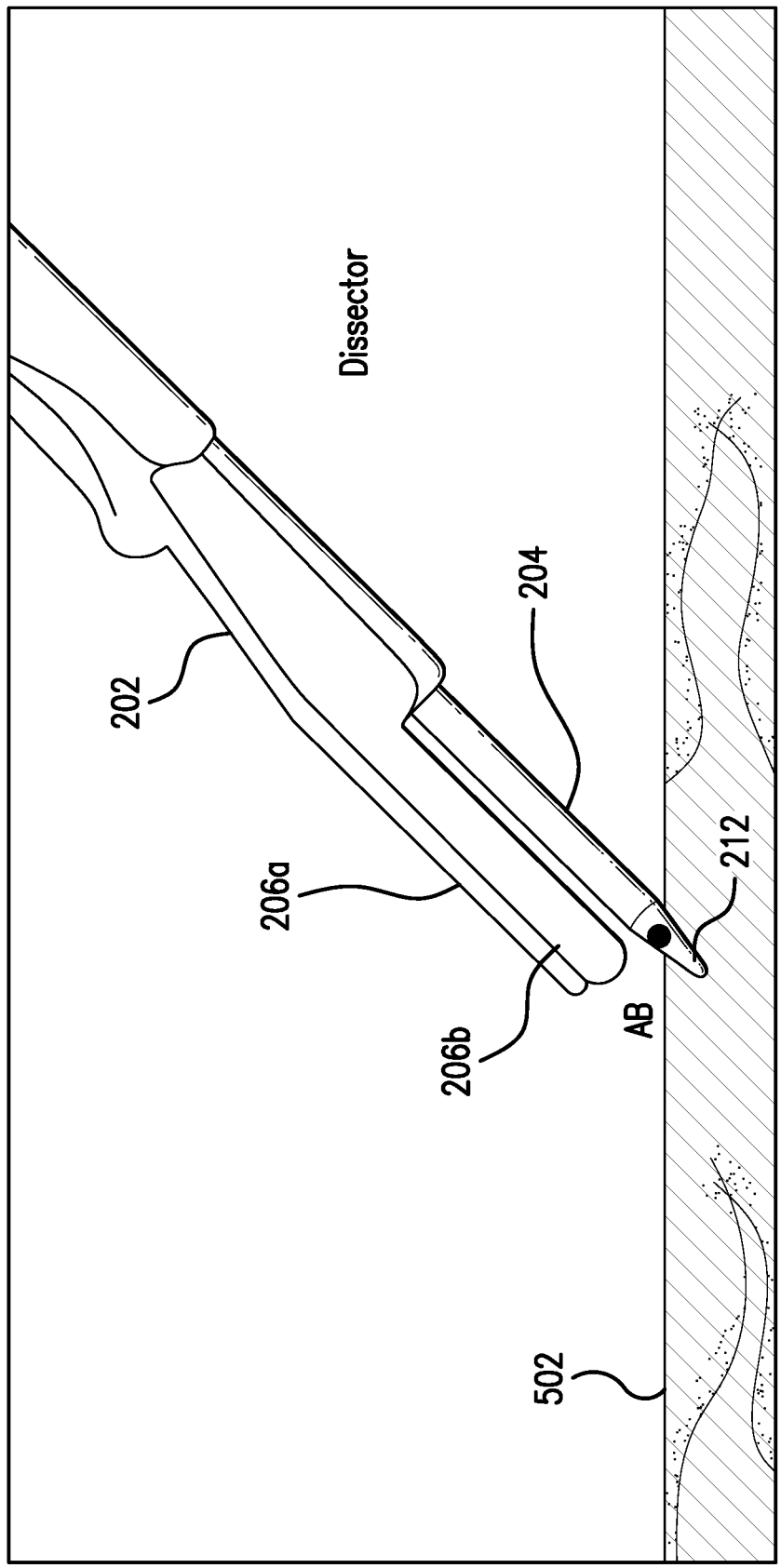
FIGS. 5A-5C illustrate a method of creating a subcutaneous pocket embodying aspects of the present disclosure.
Figure 5B:
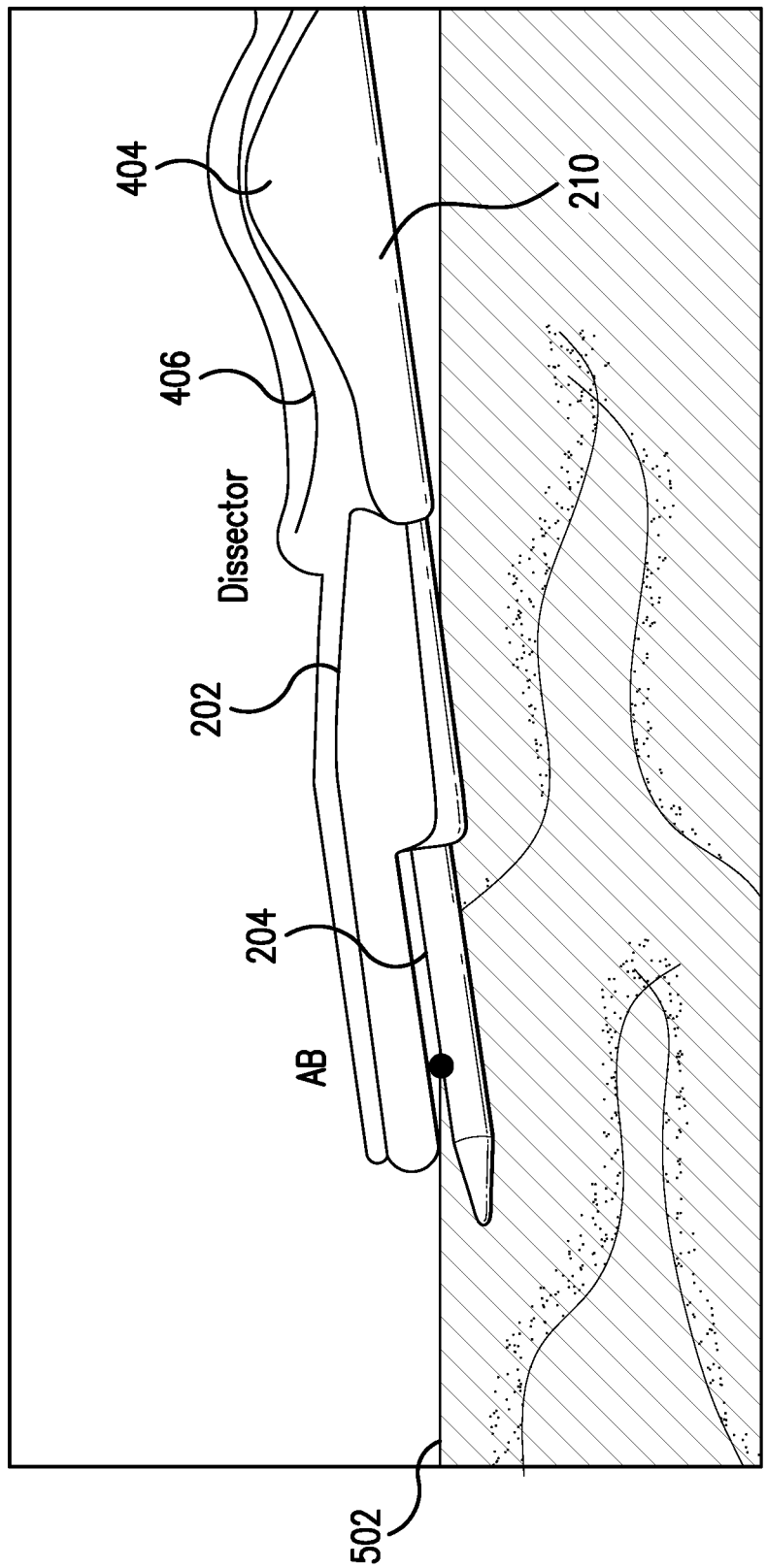
Figure 5C:
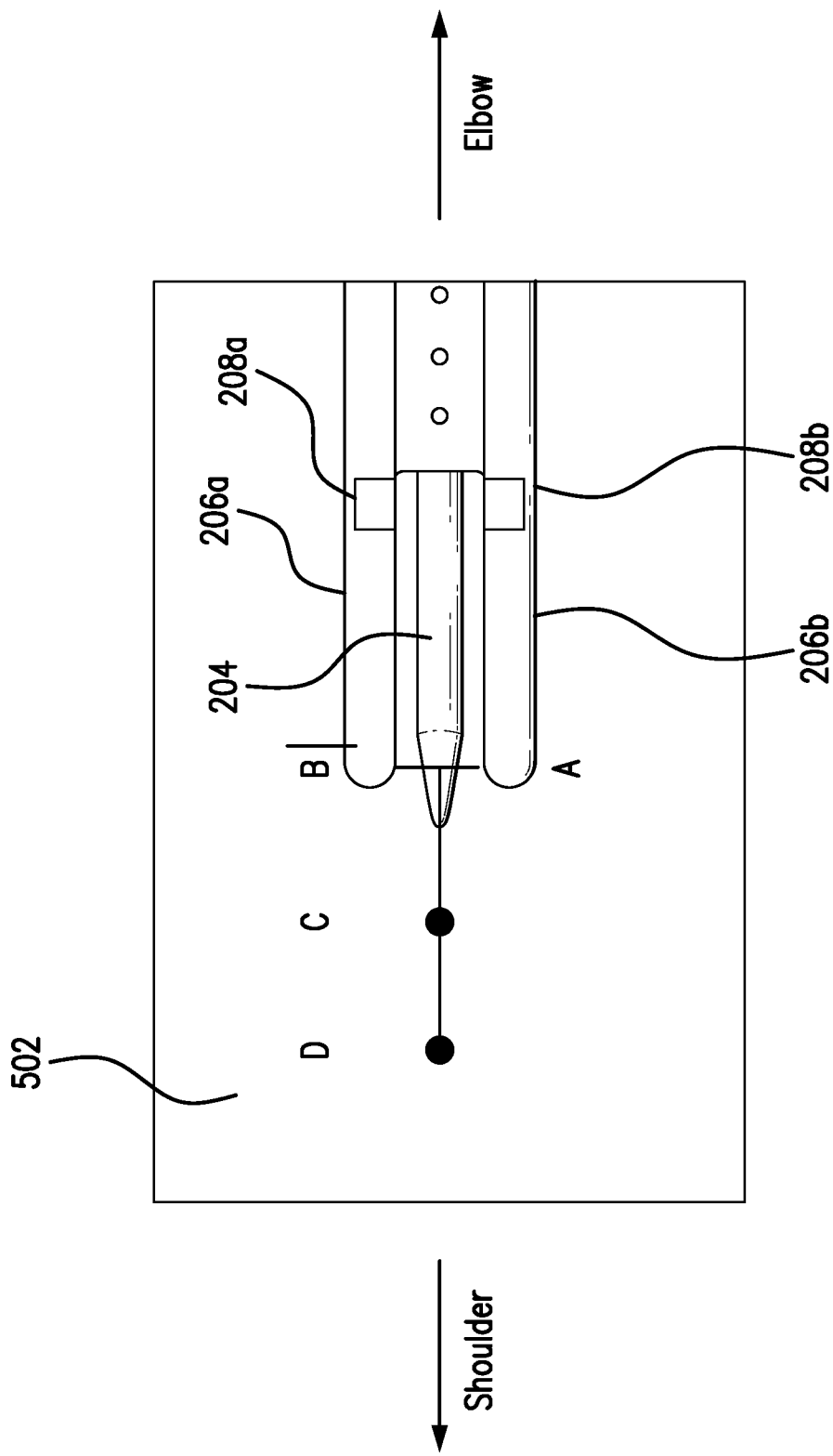

FIGS. 5A-C illustrate a method of creating a subcutaneous pocket embodying aspects of the present disclosure. In some embodiments, the tunneling tool 202 described above in FIGS. 2-4 may be used to create the subcutaneous pocket according to the method described in FIGS. 5A-C.

In some embodiments, the method may include a first step in which an incision may be made in a skin surface 502 at an insertion location for the tunneling tool 202. In some embodiments, the incision may be, for example and without limitation, 6-8 mm wide and 4-6 mm deep. However, these dimensions are not required, and some alternative embodiments may use different dimensions.

In some embodiments, the method may include a second step in which, as shown in FIG. 5A, the tip 212 of the rod 204 of the tunneling tool 202 may be inserted into the incision. In some embodiments, the tip 212 of the rod 202 may be inserted into the incision to form an angle between the tunneling tool 202 and the skin surface 502, i.e. an entry angle of the tunneling tool 202. In some embodiments, the tip 212 of the rod 202 may be inserted into the incision at, for example and without limitation, a 45 degree entry angle. In some embodiments, the tip 212 of the rod 202 may be inserted into the incision until at least one or more of the first and second prongs 206a-b contact the skin surface 502. In some embodiments, the rod 202 may be inserted into the incision until the tip 212 and the beveled portion of the rod 202 are under the skin surface 502.

In some embodiments, the method may include a third step in which, as shown in FIG. 5B, after one or more of the first and second prongs 206a-b contact the skin surface 502, the tunneling tool 202 is rotated with the tip 212 of the rod 204 inserted in the incision made in the skin surface 502 to reduce the entry angle. In some embodiments, the tunneling tool 202 may be rotated to reduce the entry angle to, for example and without limitation, 5-10 degrees. In some embodiments, the tunneling tool 202 may be rotated until a bottom surface of the tunneling tool 202 contacts the skin surface 502. In some embodiments, the user may grip the tunneling tool 202 on one or more of the side surface and top surface of the tunneling tool 202. In some embodiments, doing so may avoid creating a steep entry angle caused by a finger under a bottom surface of handle 210 or the rod 204. For example, in some embodiments, the user may grip the tunneling tool 202 using the side grip 404 on one or both sides of the handle 210, a bump 402 on a top surface the handle 210, and a depression 406 formed on the top surface of the handle 210, as described above with respect to FIGS. 4A-D.

In some embodiments, the method may include a fourth step in which, as shown in FIG. 5C, the rod 204 may be inserted further into the incision such that the rod 204 passes below the skin surface 502 and the skin surface 502 is disposed between the rod 204 and the first and second prongs 206a-b. In such embodiments, the first length indicator 208a and the second indicator 208b may indicate a length of the subcutaneous pocket formed by the rod 204. In some embodiments in which the incision is made on the skin surface 502 of an arm, the rod 204 may be inserted further into the incision in a direction towards the shoulder, while maintaining the reduced entry angle for the rod 204. In some embodiments, the rod 204 may be inserted into the incision with the skin surface 502 disposed between the rod 204 and the first and second prongs 206a-b until the incision reaches the first length indicator 208a and the second length indicator 208b. In some embodiments, after the incision reaches the first length indicator 208a and the second length indicator 208b, the rod 204 may be removed from the incision.

Figure 6:
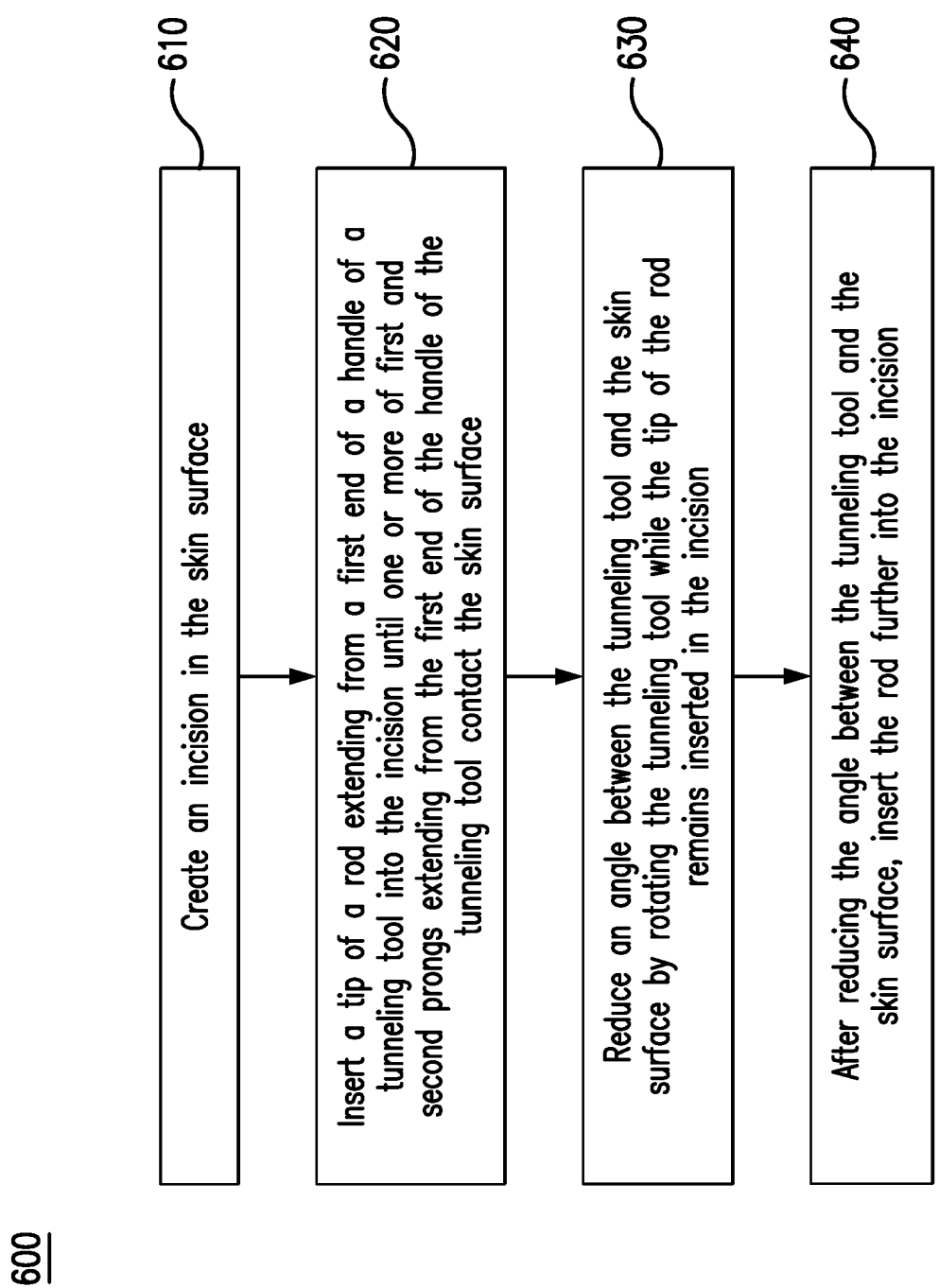
FIG. 6 illustrates a flowchart of a method for creating a subcutaneous pocket embodying aspects of the present disclosure.

FIG. 6 illustrates a flowchart of a method 600 for creating a subcutaneous pocket below a skin surface embodying aspects of the present disclosure. In some embodiments, the method 600 may include a step 610, in which an incision may be created in the skin surface.

In some embodiments, the method 600 may include step 620, in which a tip of a rod extending from a first end of a handle of a tunneling tool may be inserted into the incision until one or more of first and second prongs extending from the first end of the handle of the tunneling tool contact the skin surface. In some embodiments, the first and second prongs may limit the depth at which the rod is capable of creating the subcutaneous pocket.

In some embodiments, the method 600 may include step 630, in which an angle between the tunneling tool and the skin surface may be reduced by rotating the tunneling tool while the tip of the rod remains inserted in the incision.

In some embodiments, the method 600 may include step 640, in which after reducing the angle between the tunneling tool and the skin surface, the rod may be inserted further into the incision. In some embodiments, the rod may be inserted further into the incision such that the rod passes below the skin surface, the first and second prongs pass over the skin surface, the skin surface is disposed in a first gap between the rod and the first prong, and the skin surface is disposed in a second gap between the rod and the second prong, wherein the first and second gaps are configured to limit the angle relative to the skin surface at which rod is capable of forming the subcutaneous pocket.

In some embodiments, the method 600 may further include a step, in which the rod may be continuously inserted into the incision until the incision is aligned with a first length indicator on the first prong. In some embodiments, the method 600 may further include a step, in which the rod may be continuously inserted into the incision until the incision is aligned with a second length indicator on the first prong.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

The invention claimed is:

1. A tunneling tool for creating a subcutaneous pocket below a skin surface, the tunneling tool comprising:
    a handle;
    a rod extending from a first end of the handle and configured to create the subcutaneous pocket; and
    first and second prongs extending from the first end of the handle, wherein the first and second prongs are configured to limit the depth at which the rod is capable of creating the subcutaneous pocket, the rod extends farther from the first end of the handle than the first and second prongs, and the first prong comprises a first length indicator configured to indicate a length of the subcutaneous pocket formed by the rod,
    wherein a first gap between the rod and the first prong and a second gap between the rod and the second prong are configured to limit the angle relative to the skin surface at which rod is capable of forming the subcutaneous pocket.

2. The tunneling tool of claim 1, wherein the second prong comprises a second length indicator configured to indicate a length of the subcutaneous pocket formed by the rod.

3. The tunneling tool of claim 1, wherein the first prong and the second prong have the same length.

4. The tunneling tool of claim 1, wherein the first prong and the second prong are configured to prevent damage to the skin surface.

5. The tunneling tool of claim 1, wherein the rod comprises a dull tip.

6. The tunneling tool of claim 1, wherein the handle further comprises a bottom surface, and the first and the second prongs are located above the rod in a plane substantially parallel to the bottom surface of the handle.

7. The tunneling tool of claim 6, wherein the first prong is located at a first angle to the rod and the second prong is located at a second angle to the rod.

8. The tunneling tool of claim 1, wherein the handle further comprises a top surface comprising a circular depression configured to accommodate a finger.

9. The tunneling tool of claim 8, wherein the top surface of the handle comprises at least one or more ridges configured to accommodate another finger and a thumb.

10. The tunneling tool of claim 9, wherein the top surface of the handle comprises a ribbed surface.

11. A method of creating a subcutaneous pocket below a skin surface, the method comprising:
    creating an incision in the skin surface;
    inserting a tip of a rod extending from a first end of a handle of a tunneling tool into the incision until one or more of first and second prongs extending from the first end of the handle of the tunneling tool contact the skin surface, wherein the first and second prongs limit the depth at which the rod is capable of creating the subcutaneous pocket;
    reducing an angle between the tunneling tool and the skin surface by rotating the tunneling tool while the tip of the rod remains inserted in the incision;
    after reducing the angle between the tunneling tool and the skin surface, inserting the rod further into the incision such that the rod passes below the skin surface, the first and second prongs pass over the skin surface, the skin surface is disposed in a first gap between the rod and the first prong, and the skin surface is disposed in a second gap between the rod and the second prong, wherein the first and second gaps are configured to limit the angle relative to the skin surface at which rod is capable of forming the subcutaneous pocket; and
    further comprising continuing to insert the rod into the incision until the incision is aligned with a first length indicator on the first prong.

12. The method of claim 11, continuing to insert the rod into the incision until the incision is aligned with a second length indicator on the second prong.

13. The method of claim 11, wherein inserting the rod further into the incision comprises rocking the tunneling tool side to side thereby creating a rotating motion along a longitudinal axis of the rod to facilitate the insertion.

14. The method of claim 13, wherein the handle further comprises a bottom surface, and the first and the second prongs are located above the rod in a plane substantially parallel to the bottom surface of the handle.

15. The method of claim 14, wherein the first prong is located at a first angle to the rod and the second prong is located at a second angle to the rod, and wherein the location of the first and second prong in relation to the rod facilitates rocking the tunneling tool side to side.

16. A tunneling tool for creating a subcutaneous pocket below a skin surface, the tunneling tool comprising:
    a handle;
    a rod extending from a first end of the handle and configured to create the subcutaneous pocket; and
    first and second prongs extending from the first end of the handle, wherein the rod extends farther from the first end of the handle than the first and second prongs, the first prong comprises a first length indicator configured to indicate a length of the subcutaneous pocket formed by the rod, and the second prong comprises a second length indicator configured to indicate the length of the subcutaneous pocket formed by the rod,
    wherein a first gap between the rod and the first prong and a second gap between the rod and the second prong are configured to limit the angle relative to the skin surface at which rod is capable of forming the subcutaneous pocket.

17. The tunneling tool of claim 16, wherein the first prong and the second prong have the same length.

18. The tunneling tool of claim 16, wherein the first prong and the second prong are configured to prevent damage to the skin surface.

19. The tunneling tool of claim 16, wherein the rod comprises a dull tip.

20. The tunneling tool of claim 16, wherein the handle further comprises a bottom surface, and the first and the second prongs are located above the rod in a plane substantially parallel to the bottom surface of the handle.

21. The tunneling tool of claim 20, wherein the first prong is located at a first angle to the rod and the second prong is located at a second angle to the rod.

22. The tunneling tool of claim 16, wherein the handle further comprises a top surface comprising a circular depression configured to accommodate a finger.

23. The tunneling tool of claim 22, wherein the top surface of the handle comprises at least one or more ridges configured to accommodate another finger and a thumb.

24. The tunneling tool of claim 22, wherein the top surface of the handle comprises a ribbed surface.

25. A method of creating a subcutaneous pocket below a skin surface, the method comprising:
creating an incision in the skin surface;
inserting a tip of a rod extending from a first end of a handle of a tunneling tool into the incision until one or more of first and second prongs extending from the first end of the handle of the tunneling tool contact the skin surface;
reducing an angle between the tunneling tool and the skin surface by rotating the tunneling tool while the tip of the rod remains inserted in the incision;
after reducing the angle between the tunneling tool and the skin surface, inserting the rod further into the incision such that the rod passes below the skin surface, the first and second prongs pass over the skin surface, the skin surface is disposed in a first gap between the rod and the first prong, and the skin surface is disposed in a second gap between the rod and the second prong, wherein the first and second gaps are configured to limit the angle relative to the skin surface at which rod is capable of forming the subcutaneous pocket; and
continuing to insert the rod into the incision until the incision is aligned with at least one of a first length indicator on the first prong and a second length indicator on the second prong, wherein the first length indicator indicates a length of the subcutaneous pocket formed by the rod, and the second length indicator indicates the length of the subcutaneous pocket formed by the rod.

26. The method of claim 25, wherein inserting the rod further into the incision comprises rocking the tunneling tool side to side thereby creating a rotating motion along a longitudinal axis of the rod to facilitate the insertion.

27. The tunneling tool of claim 26, wherein the handle further comprises a bottom surface, and the first and the second prongs are located above the rod in a plane substantially parallel to the bottom surface of the handle.

28. The method of claim 27, wherein the first prong is located at a first angle to the rod and the second prong is located at a second angle to the rod, and wherein the location of the first and second prong in relation to the rod facilitates rocking the tunneling tool side to side.

* * * * *